United States Patent
Huang et al.

(10) Patent No.: US 8,130,908 B2
(45) Date of Patent: Mar. 6, 2012

(54) X-RAY DIFFRACTION APPARATUS AND TECHNIQUE FOR MEASURING GRAIN ORIENTATION USING X-RAY FOCUSING OPTIC

(75) Inventors: Huapeng Huang, Ellicott City, MD (US); Alexei Vershinin, Schenectady, NY (US)

(73) Assignee: X-Ray Optical Systems, Inc., East Greenbrush, NY (US)

( * ) Notice: Subject to any disclaimer, the term of this patent is extended or adjusted under 35 U.S.C. 154(b) by 213 days.

(21) Appl. No.: 12/710,827

(22) Filed: Feb. 23, 2010

(65) Prior Publication Data

US 2011/0038457 A1 Feb. 17, 2011

Related U.S. Application Data

(60) Provisional application No. 61/154,572, filed on Feb. 23, 2009.

(51) Int. Cl.
*G01N 23/207* (2006.01)
(52) U.S. Cl. .......................................................... 378/73
(58) Field of Classification Search ............... 378/70–90
See application file for complete search history.

(56) References Cited

U.S. PATENT DOCUMENTS

| | | |
|---|---|---|
| 5,175,755 A | 12/1992 | Kumakhov |
| 5,192,869 A | 3/1993 | Kumakhov |
| 5,497,008 A | 3/1996 | Kumakhov |
| 5,570,408 A | 10/1996 | Gibson |
| 5,604,353 A | 2/1997 | Gibson et al. |
| 5,745,547 A | 4/1998 | Xiao |
| 6,285,506 B1 | 9/2001 | Chen |
| 7,035,374 B2 | 4/2006 | Chen |
| 7,110,506 B2 | 9/2006 | Radley et al. |
| 7,209,545 B2 | 4/2007 | Radley et al. |
| 7,257,193 B2 | 8/2007 | Radley et al. |

*Primary Examiner* — Courtney Thomas
(74) *Attorney, Agent, or Firm* — Jeff Klembczyk, Esq.; Kevin P. Radigan, Esq.; Heslin Rothenberg Farley & Mesiti P.C.

(57) ABSTRACT

An x-ray diffraction apparatus for measuring crystal orientation of a multiple grain sample. An x-ray excitation path is provided having a focusing optic for collecting x-rays from an x-ray source and redirecting the collected x-rays into an x-ray beam converging on a single grain of the multiple grain sample. At least one point detector and the sample are rotated relative to each other; and a grain orientation is obtained based upon diffraction patterns collected from first and second grain crystal planes within the apparatus.

12 Claims, 10 Drawing Sheets

FIG. 13

X-RAY DIFFRACTION APPARATUS AND TECHNIQUE FOR MEASURING GRAIN ORIENTATION USING X-RAY FOCUSING OPTIC

CROSS-REFERENCE TO RELATED APPLICATIONS

This application claims the benefit of U.S. provisional patent application Ser. No. 61/154,572, filed Feb. 23, 2009, which is hereby incorporated herein by reference in its entirety.

STATEMENT OF GOVERNMENT INTEREST

Certain portions of this invention were made under U.S. Department of the Air Force Contact No. FA8103-07-C-0008. The U.S. Government has certain rights in this invention.

TECHNICAL FIELD

This invention relates in general to x-ray diffraction (XRD) techniques and analyzers. More particularly, this invention relates to an improved x-ray diffraction technique and analyzer for analyzing grain orientation in multiple grain materials, e.g., directionally solidified alloys used in turbine blades.

BACKGROUND OF THE INVENTION

Directionally solidified (DS) nickel superalloys are commonly used in turbine blades for high temperature aircraft and space propulsion engines and land-based, high-efficiency power generating plants. Casting of these parts does not always result in perfect crystal grain orientation, which is critical for performance under high temperature conditions. Engine failures, including aircraft mishaps, have heightened the emphasis on efficient and direct measurement of grain orientation in turbine blades.

Conventional chemical etching, visual inspection, and/or laboratory based x-ray analysis techniques based on Laue Diffraction are unsuitable and/or cost prohibitive for quality control of an entire turbine blade. As one example, conventional X-ray Laue Diffraction (XRD) can be used to determine single crystal grain orientation. The conventional approach uses an X-ray area detector to collect an XRD Laue pattern produced by an X-ray beam incident on a sample, and determining the grain orientation by processing this collected Laue pattern. However, certain problems exist when using the Laue method to determine grain orientation for DS blades. DS blades may consist of several, single-crystal grains. Therefore, the diffraction pattern is usually generated from multiple grains and the images become complex and difficult to analyze.

What is required, therefore, are improved techniques for measurement of grain orientation of multiple grain samples.

SUMMARY OF THE INVENTION

The shortcomings of the prior art are overcome and additional advantages are provided the present invention which in one aspect is an x-ray diffraction apparatus for measuring crystal orientation of a multiple grain sample. An x-ray excitation path is provided having a focusing optic for collecting x-rays from an x-ray source and redirecting the collected x-rays into an x-ray beam converging on a single grain of the multiple grain sample. A point detector and the sample are rotated relative to each other; and the grain orientation is obtained based upon diffraction patterns collected from first and second grain crystal planes within the apparatus.

A second point detector may also be provided, wherein the first point detector collects a diffraction pattern from the first crystal plane, and the second point detector collects a diffraction pattern from the second crystal plane.

The sample may be placed upon a rotation stage to facilitate collection of diffraction patterns from the first and second crystal planes by the first point detector, and/or the detector(s) may be mounted on rotation stage(s), to facilitate collection of diffraction patterns from the first and second crystal planes by the detector(s).

In one embodiment, the focusing optic comprises a polycapillary optic, having an output focused beam spot size of about 300 μm or smaller, which can effectively excite a single grain of multiple grain turbine blade sample.

Further, additional features and advantages are realized through the techniques of the present invention. Other embodiments and aspects of the invention are described in detail herein and are considered a part of the claimed invention.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

DESCRIPTION OF THE INVENTION

Disclosed herein is a compact, low-power, focusing beam x-ray diffraction technique, and associated analyzer, that can directly and nondestructively measure each individual grain orientation in a sample having multiple grains, in e.g., a DS turbine blade. The analyzer is especially suitable for use in factory production lines, or in the field. The technique is enabled by proprietary focusing x-ray optics, and a highly stable and reliable low power X-Beam system, coupled with a novel approach to determine grain orientation by diffraction beam directions from selected crystal planes.

Figure 1:
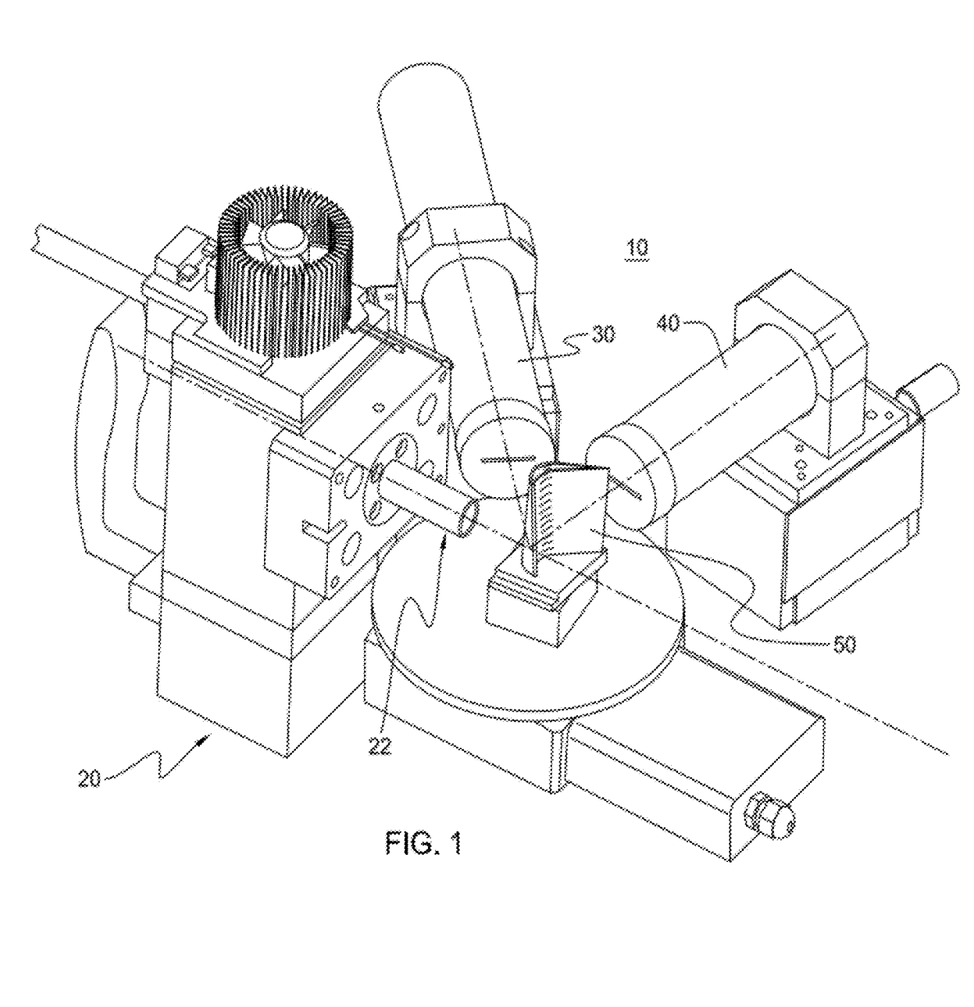
FIG. 1 depicts an exemplary x-ray diffraction system, in accordance with one aspect of the present invention.

FIG. 1 depicts an exemplary diffraction analyzer 10, analyzing a sample 50 (e.g., turbine blade) in accordance with one aspect of the present invention. Analyzer 10 includes an x-ray source 20, and coupled x-ray optic 22, for directing a converging, focused x-ray excitation beam toward sample 50, preferably small enough to excite only a single grain of a multiple grain sample 50. Detectors 30 and 40 are positioned to receive diffraction patterns from sample 50. The detectors, source, and/or sample may be placed on movement stages to effect the positional changes discussed elsewhere herein. "Relative" motion between two components is used herein to broadly connote movement by any or all of the structures relative to each other.

This exemplary analyzer includes, for example, a focusing optic for excitation and a point detector to rapidly determine grain orientation and, whether the grain orientation is acceptable or not. The focusing optic's output focused beam spot size can be, e.g., ~300 µm or smaller, e.g., small enough to scan individual grains. The range of spot sizes contemplated by this invention is several mm to as small as 200 µm. Such optics include, for example, curved crystal monochromating optics such as those disclosed in commonly assigned U.S. Pat. Nos. 6,285,506; 6,317,483; and 7,035,374; and/or multilayer optics; and/or polycapillary optics such as those disclosed in commonly assigned U.S. Pat. Nos. 5,192,869; 5,175,755; 5,497,008; 5,745,547; 5,570,408; and 5,604,353. Optic/source combinations such as those disclosed in commonly assigned U.S. Pat. Nos. 7,110,506; 7,209,545; and 7,257,193 are also useable, which disclose lower cost, electron bombardment tubes coupled to an optic. Each of the above-noted patents is incorporated herein by reference in its entirety.

This new approach enables measurement of one single grain at a time on DS blades. Therefore, the problems that plague the Laue technique, when used for multiple grain samples, do not occur.

Figure 2:
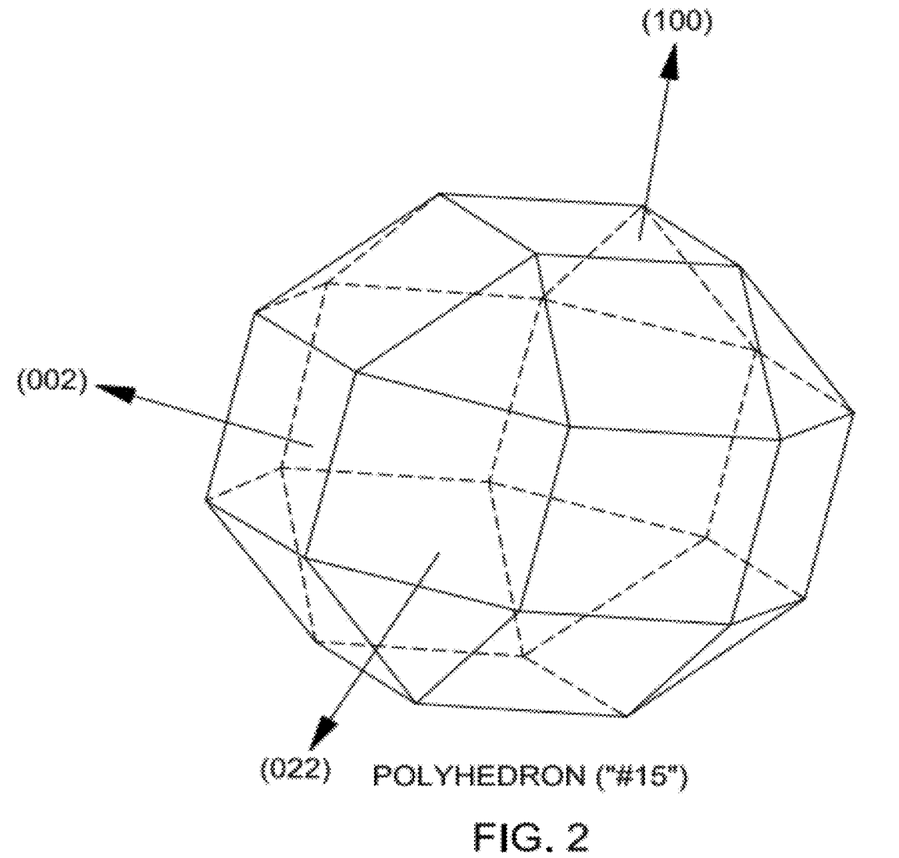
FIG. 2 is a polyhedron schematic of an exemplary sample crystal structure having various grain crystal planes.

In accordance with the present invention, and with reference to the polyhedron schematic of an exemplary sample crystal structure in FIG. 2, if, for example, both (002) and (022) plane orientations are determined, then the grain growth orientation (100) can also be determined in accordance with the present invention. To effect these measurements, a sample is rotated so that each grain can be measured in a way to meet the Bragg diffraction condition. For example, the (002) plane and the (022) plane diffraction beam direction for the grain orientation determination can be measured. The angular alignment position for (002) plane and (022) plane diffraction, combined with the diffraction beam direction, comprise inputs for the grain orientation calculation.

In one exemplary system design, the point detectors are mounted at the 2θ angles of 81° and 133°. These are the angular 2θ positions for (002) plane and (022) plane diffraction. A sample is mounted on a rotational scanning base for the diffraction peak search, and the data collected, for each individual grain.

Figure 3A:
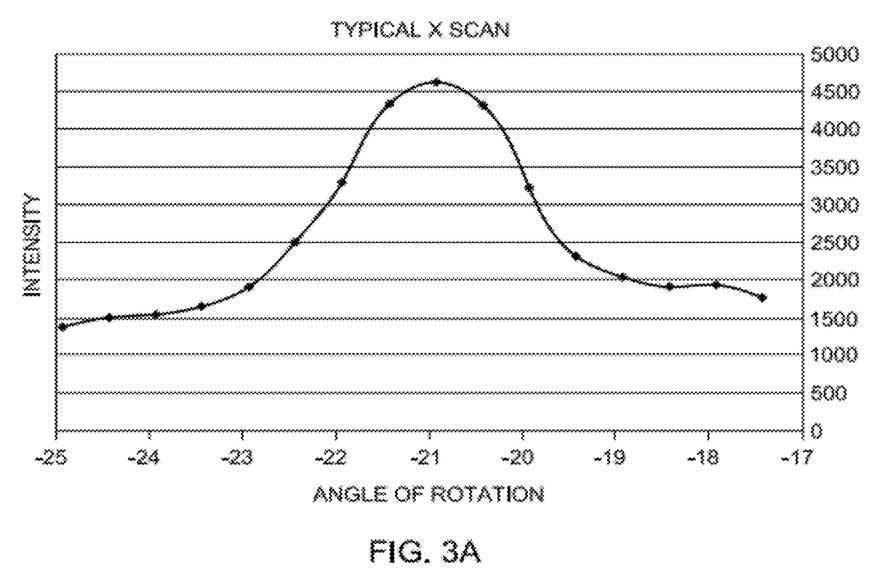
FIGS. 3a-b show typical diffraction peak search rotation scan (X) and peak vertical position scan (Y) intensity curves.
Figure 3B:
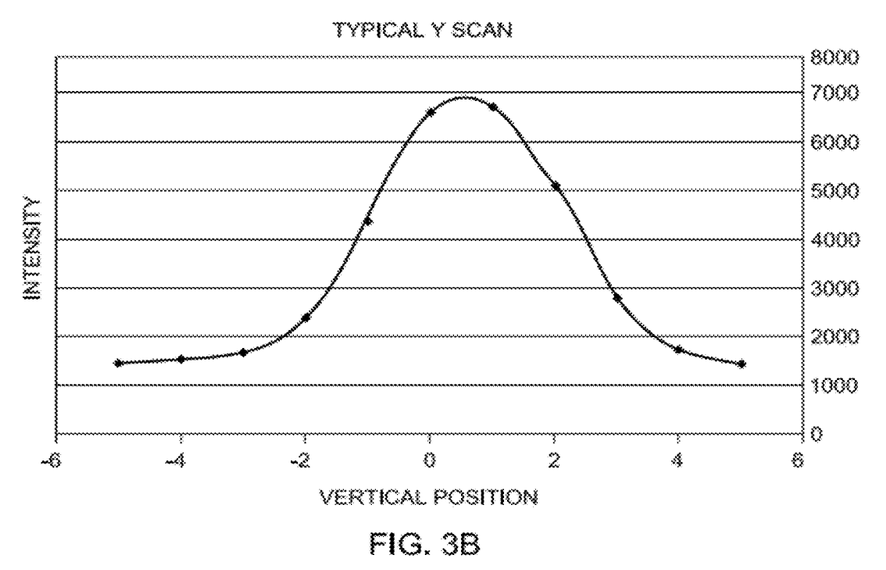
Figure 4A:
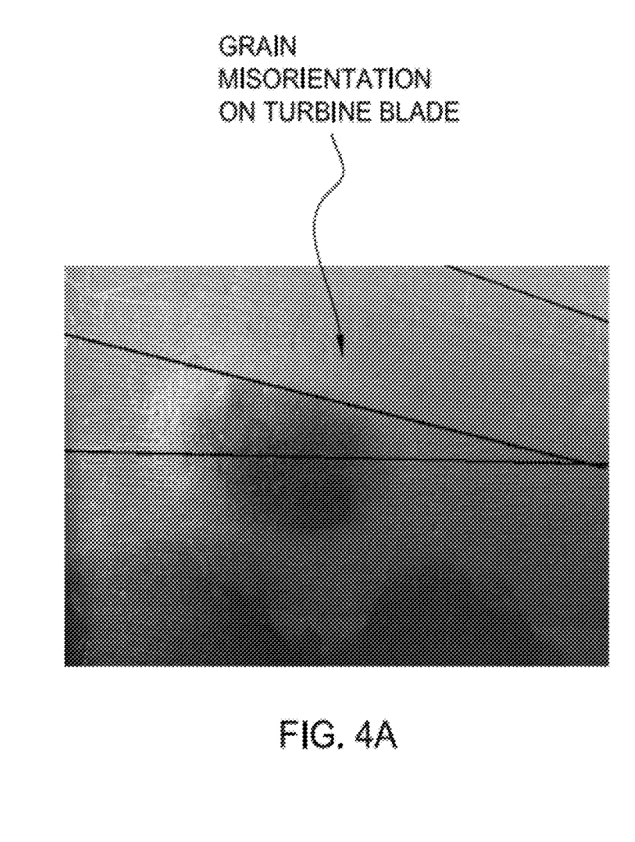
FIGS. 4a-b are photographs of a turbine blade surface with a mis-oriented grain.
Figure 4B:
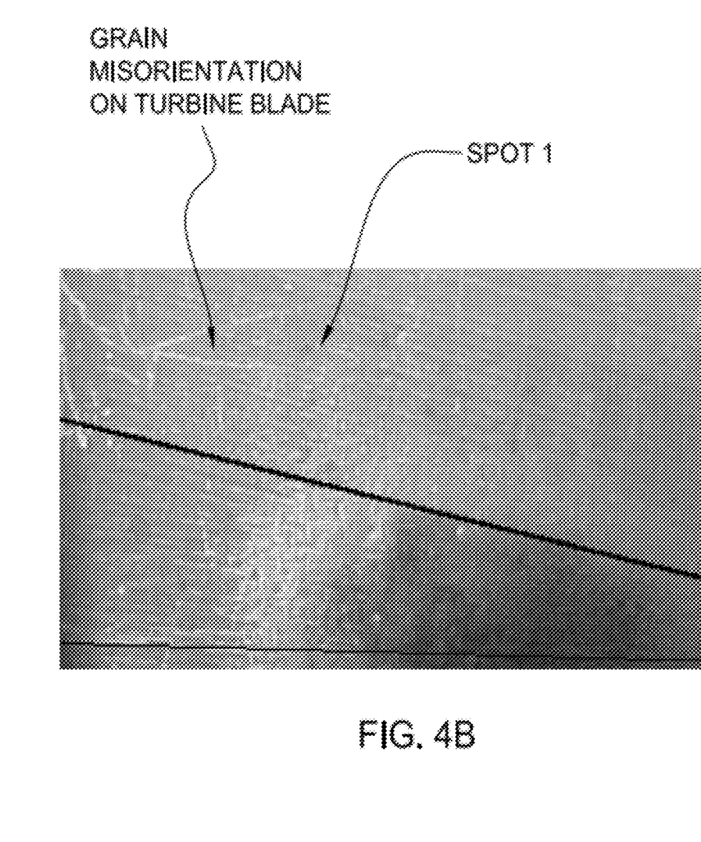

Obtaining turbine grain orientation using one or more point detectors is discussed below, using a NaI point detector. This detector has large capture area, up to 2 inches in diameter, high sensitivity, high counting rate, low energy-resolution and low cost. Two diffraction spots for each of four blades were chosen and tested. FIGS. 3a-b show typical diffraction peak search rotation scan (X) and peak vertical position scan (Y) intensity curves. Table 1 shows the calculated values for mis-oriented grains of four selected turbine blades. The spot is a location on the turbine blade near the physical transition from the exposed blade to the exposed platform surface. Blade 1 is shown in the photograph of FIGS. 4a-b with a mis-oriented crystal.

TABLE 1

Mis-orientation calculations for Blades 1-4

| Blade | Spot | Mis-orientation (degrees) |
|---|---|---|
| 1 | 1 | 9.5 |
| 1 | 2 | 3 |
| 2 | 1 | 5.1 |
| 2 | 2 | 1.8 |
| 3 | 1 | ## |
| 3 | 2 | 3.3 |
| 4 | 1 | 16 |
| 4 | 2 | 4.1 |

Table 1 shows that blade 1, spot 1, and blade 4, spot 1 have the largest mis-orientation angles. This was also confirmed from a visual inspection, i.e., both turbine blade number 1 spot 1 and turbine blade number 4 spot 1 had visible signs of mis-orientation.

Figure 5A:
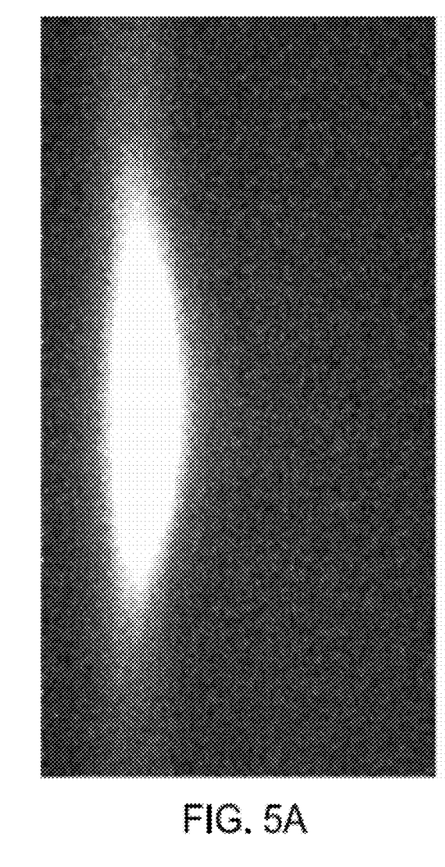
FIGS. 5a-b show exemplary diffraction patterns from a turbine blade and a silicon wafer.
Figure 5B:
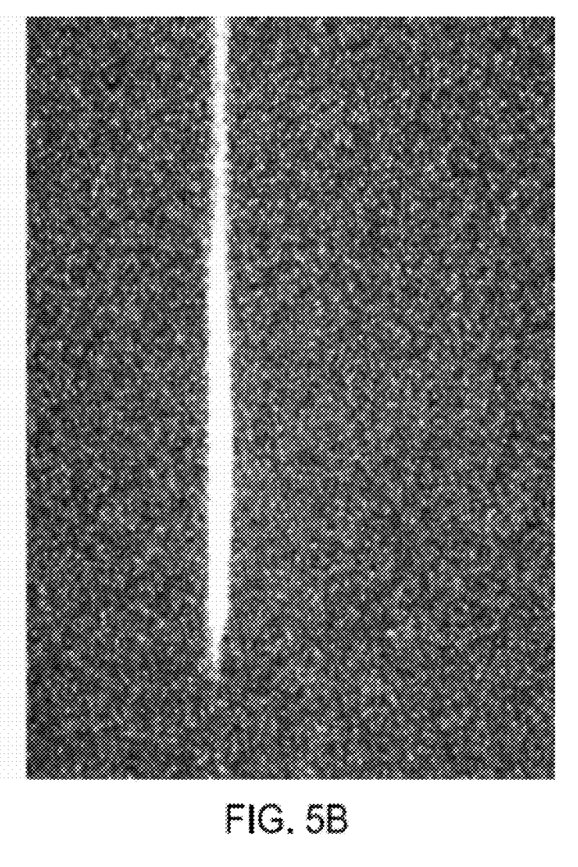

In practice, DS turbine blades can have complicated crystal structure and grain orientation distributions. These blades may not have a high crystal quality, the grain size is limited, and there may be a large mosaic spread. Taken together, these characteristics confirm what is described herein, that turbine blade diffraction patterns are not similar to silicon wafer diffraction spots. As an example, FIGS. 5a-b compare diffraction spots obtained from a turbine blade (a) and a silicon wafer (b).

The XRD measurements disclosed herein can provide important crystal structure information about turbine blade samples. Two important conclusions were made. First, it was concluded that the DS blades have Ni based cubic FCC structure, instead of $Ni_3Al$. Second, it was concluded that the diffraction spots may originate only from 002, 111 and 022 crystal planes, using $Cr\ K_\alpha$ x-ray excitation.

Figure 6A:
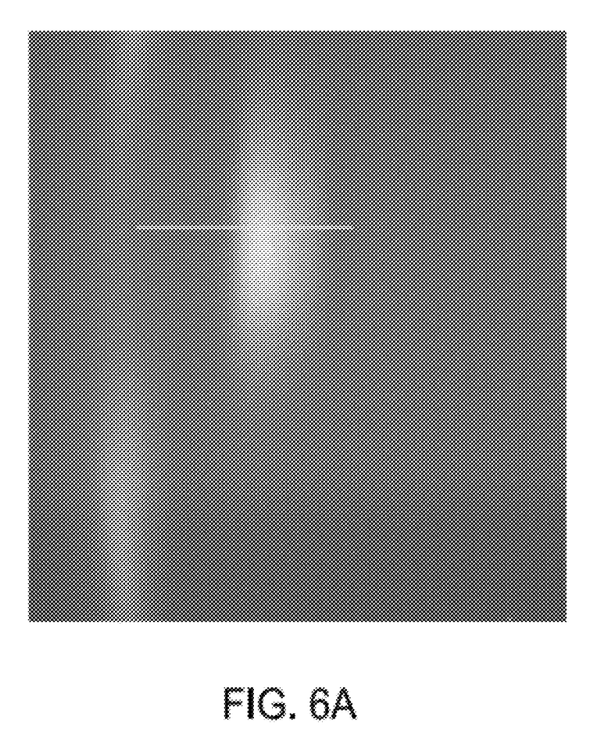
FIGS. 6a-b show exemplary experimental and simulated diffraction patterns.
Figure 6B:
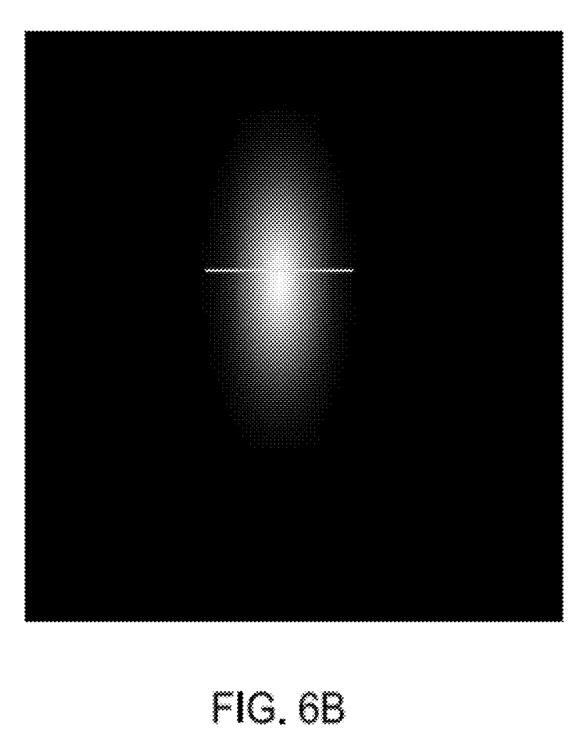

Simulation results can be compared to results obtained using the analyzer disclosed herein, to validate this technique of measuring grain mis-orientation in turbine blades. For example, FIGS. 6a-b show two diffraction images: FIG. 6a shows a diffraction pattern obtained using the XRD system disclosed herein; and FIG. 6b shows a diffraction pattern obtained from simulation.

This simulation pattern was generated based on the following conditions:
1. Crystal plane was [0 –2 0]
2. Crystal angular position was $\alpha=40.6°$
3. Crystal mosaicity was 2.5°
4. Crystal angular position was for $\alpha=40.6°$, $\beta=0°$
5. Crystal grain size was 1 mm
6. Incident beam divergence was 3.7°
7. Incident beam was $Cr\ K_\alpha$
8. Detector active area was 62 mm×62 mm, with resolution 62/512 mm
9. Detector distance from sample was 92 mm,
10. Detector angular position was 80°
11. Detector height offset was 5 mm.

The residual difference between the real experimental data and the simulation pattern arises from the poor crystal quality of the DS turbine blade grain and the irregular grain shape. However, because the primary objective is to determine the grain orientation, this simulation pattern can provide enough information for this purpose.

Figure 7:
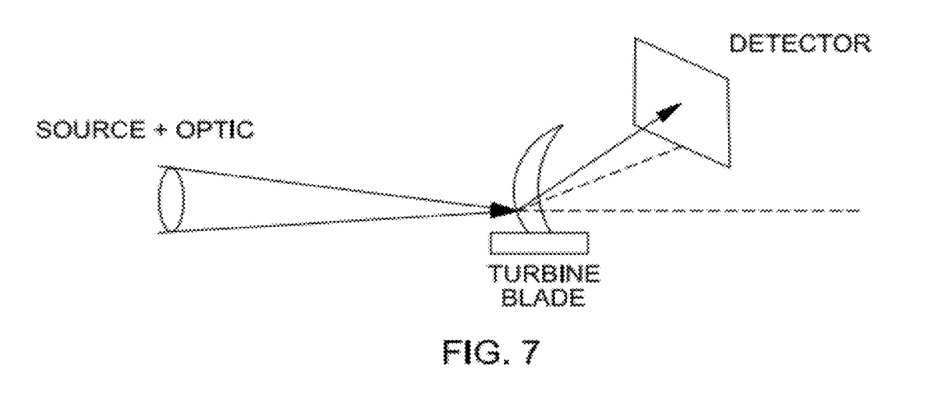
FIG. 7 is a schematic of an XRD analyzer showing a detector able to rotate around a perpendicular axis through the sample measurement point, and also with an adjustable height, in accordance with the present invention.

Further analysis using such simulations are possible, to validate the corresponding analyzer configurations, all of which fall within the scope of the present invention. For example, and with reference to FIG. 7, a detector may be rotated along a perpendicular axis through the sample measurement point. Its height can also be adjusted. It was assumed the incident focusing spot hit right on the turbine blade measurement position.

Figure 8:
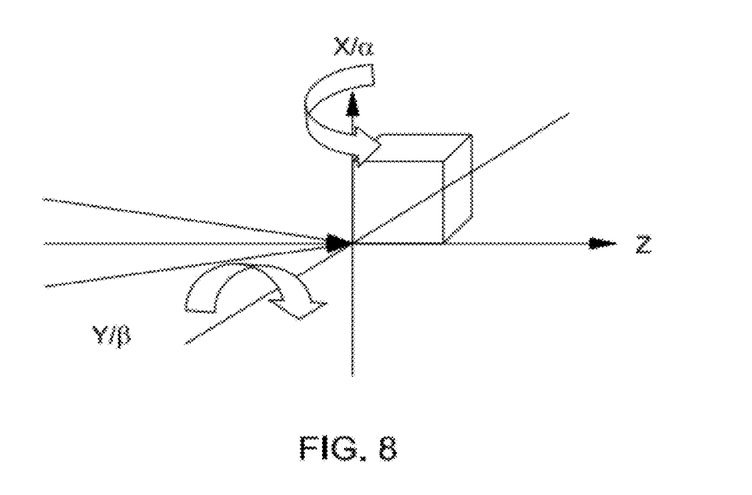
FIG. 8 is a schematic of an exemplary coordinate system, with orthogonal X, Y and Z axes and $\alpha$ and $\beta$ rotation axes for angular alignment of an exemplary turbine blade crystal sample.

The system can be defined by orthogonal X, Y and Z axes, and $\alpha$ and $\beta$ rotation axes, for angular alignment of the turbine blade crystal, as shown in FIG. 8. The initial angular position for the crystal is $\alpha=0$, $\beta=0$.

Figure 9:
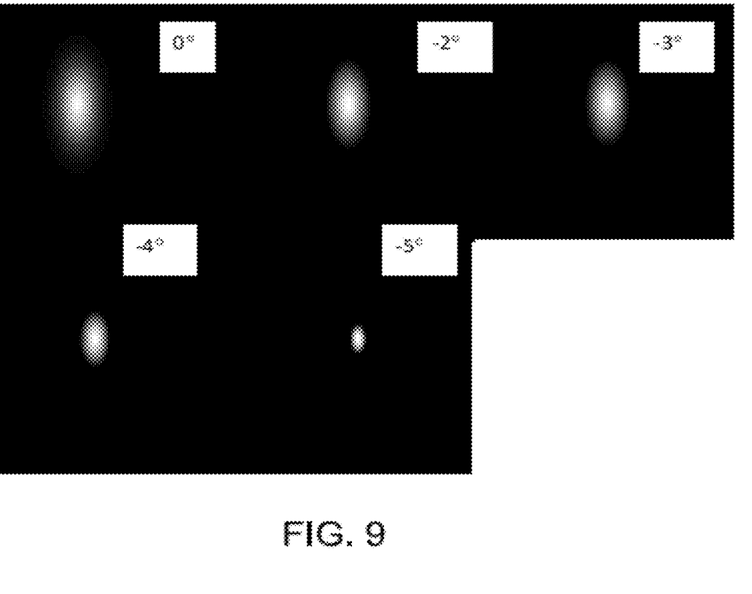
FIG. 9 depicts simulation images for an $\alpha$ angle offset of 0, −2, −3, −4, and −5 degrees.

A systematic simulation measurement validated XRD patterns for directionally solidified (DS) turbine blades according to the techniques disclosed herein. First, a series of simulation patterns can be generated with sample crystal angular misalignments. Both the diffraction intensity and the diffraction spot angular position changes according to the crystal misalignment. However, it is not a simple issue to directly use these changes to locate the crystal orientation. In this case, $\alpha$ was directly correspondent to the incident $\theta$ angle, and $\beta$ was kept equal to 0, so the diffraction spot intensity and angular position would change to meet the Bragg conditions whenever the crystal angular position is changed. The $\alpha$ angular offsets were 0, $-2°$, $-3°$, $-4°$, and $-5°$ for the following simulation patterns, and FIG. 9 shows these simulation images.

Figure 10:
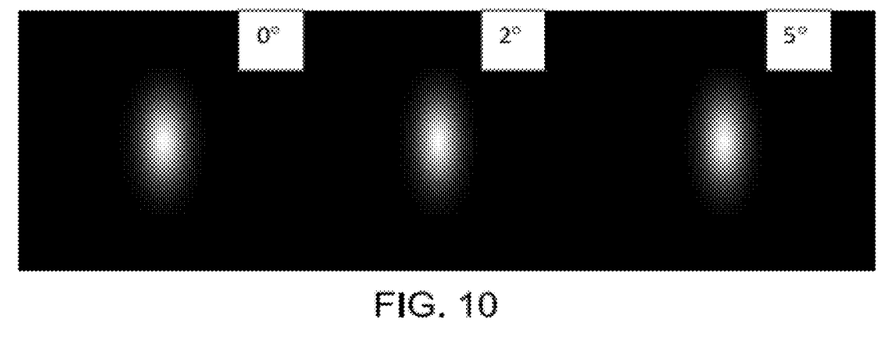
FIG. 10 depicts images for detector angular position at 80 degrees, with a $\beta$ angle offset of 0, 2 and 5 degrees.

Another important analysis involves analyzing diffraction angular position changes with the $\beta$ angle, which can be used as an indicator of turbine blade grain mis-orientation. From geometrical analysis, it can be assumed that $\beta$ changes do not vary position on the detector for the 002 diffraction spot, however, it should have impact on both 022 and 111 diffraction spots. In FIG. 10, simulation images are shown for the 002 plane with different $\beta$ angles.

As can be seen from FIG. 10, there is no visible change in diffraction from the 002 diffraction plane by varying the $\beta$ angle.

Figure 11:
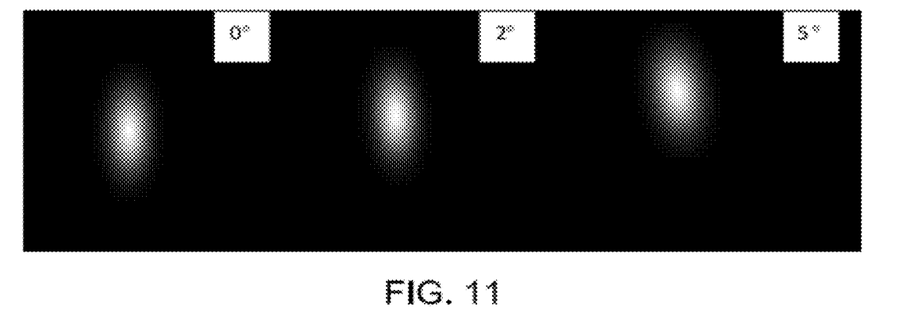
FIG. 11 depicts images for detector angular position at 130 degrees, with a $\beta$ angle offset of 0, 2, and 5 degrees.

In FIG. 11, simulation patterns are shown for the 022 plane with different angles. The diffraction spot for the 022 plane changes its height by increasing the angle offset.

Figure 12:
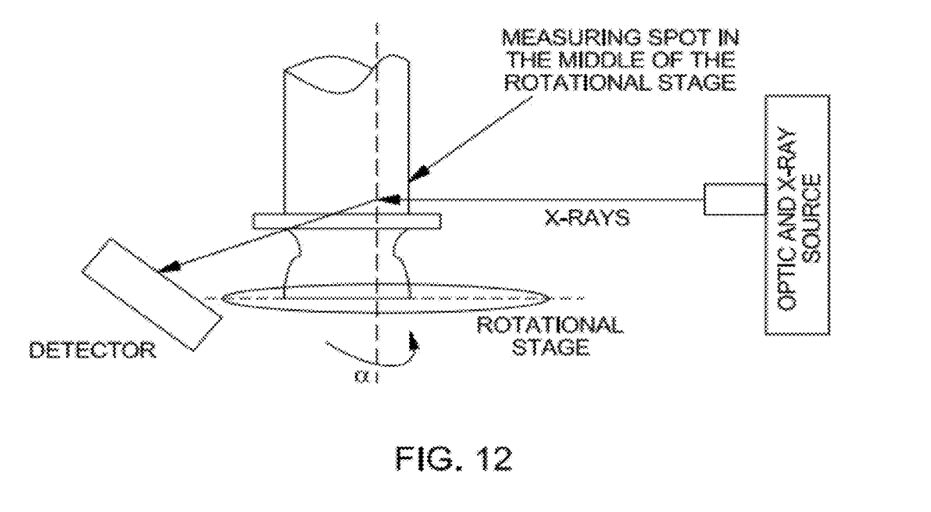
FIG. 12 is a schematic of an XRD analyzer, showing only $\alpha$ angular scans, in accordance with the present invention.

A new data collection and processing procedure is also disclosed in accordance with the present invention. One significant aspect of this approach is that only $\alpha$ angular scans are performed for the turbine blade sample diffraction alignment, as shown in FIG. 12. This is based on the analysis of a series of XRD diffraction patterns, which show that for most turbine blade samples, $\beta$ angular scans for searching diffraction spots can be avoided. Based on the analysis, a new procedure has been developed for the orientation measurements:

1. Find a diffraction spot for 002 plane ($2\theta$ angle=81.1°).
   a. Insert a turbine blade into the holder.
   b. Align a turbine blade, so the measuring spot on a turbine blade is aligned with the center axis of the rotational stage. The alignment is performed using two lasers.
   c. Set a detector at the appropriate position to capture 002 plane diffraction.
   d. Record the detector angular position.
   e. Perform a scan to search for the diffraction spot. The range for a sample to be rotated is 70° with a step size of 5°, acquiring time per step is 1-5 seconds and the power is 40 kV, 1 mA.
   f. After finding a diffraction spot, a pinhole is placed with diameter of 1.2 mm at front of the optic.
   g. Maximize intensity for a diffraction spot.
   h. Record the diffraction image, center position.
2. Find the second diffraction spot for 022 plane ($2\theta=133.8°$).
   a. Rotate the detector to capture diffraction from the 022 plane.
   b. Record the detector angular position.
   c. Perform an a scan to search for the diffraction spot.
   d. After finding a diffraction spot, place a pinhole with diameter of 1.2 mm a front of the optic.
   e. Maximize intensity for the diffraction spot.
   f. Record the rotated angle for the turbine blade and the diffraction image spot position.
   g. Plug into the program.
      i. Distance between detector and a sample.
      ii. Detector angular position for two diffraction spots
      iii. Rotation angle $\Delta\alpha$ from spot 1 and spot 2.
      iv. X, Y position on the detector for the diffraction spot 1.
      v. X, Y position on the detector for the diffraction spot 2.
   h. The program will then calculate the orientation or mis-orientation of the grain.

As shown above, 8 parameters are required for the orientation calculation. The mathematic formulas to calculate the grain orientation are as follows:

(I) Diffraction Vector Calculation $$V\_1 := \begin{pmatrix} X\_1 \\ -D \cdot \sin(A\_1) - Y\_1 \cdot \cos(A\_1) \\ D \cdot \cos(A\_1) + Y\_1 \cdot \sin(A\_1) \end{pmatrix}$$

(II) Crystal Plane Normal Vector Calculation $$N\_2 := \frac{\left[ \begin{pmatrix} 0 \\ 0 \\ 1 \end{pmatrix} + \frac{V\_2}{|V\_2|} \right]}{2}$$

(III) Coordinate System Transformation $$Tran := \begin{pmatrix} \cos(beta) & \sin(alpha) \cdot \sin(beta) & -\cos(alpha) \cdot \sin(beta) \\ 0 & \cos(alpha) & \sin(alpha) \\ \sin(beta) & -\sin(alpha) \cdot \cos(beta) & \cos(alpha) \cdot \cos(beta) \end{pmatrix}$$

(IV) Mis-Orientation Calculation $$Off\_Ori := a\cos\left(\frac{G\_V_{0,0}}{|G\_V|}\right) \cdot \frac{180}{\pi}$$

The calculations are on vectors, and for each calculation the coordinate system should be determined.

A series of experimental data was obtained from a turbine blade having grain mis-orientations. The raw data and orientation calculations are shown in Table 2.

TABLE 2

Turbine blade measurement raw data:

| Plane | Needed to turn | Det position | X Value | Y Value |
|-------|----------------|--------------|---------|---------|
| Sample 4, Location 1 | | | | |
| 002 | 0 | +15 | 212 | 80 |
| 022 | 62 | −20 | 62 | 250 |
| Sample 4, Location 2 | | | | |
| 002 | 0 | +15 | 258 | 125 |
| 022 | 23 | −25 | 52 | 175, det higher +26 mm |
| Sample 4, Location 3 | | | | |
| 002 | 0 | +15 | 239 | 350 |
| 022 | 56 | −20 | 51 | 400 |
| Sample 4, Location 4 | | | | |
| 002 | 0 | +15 | 242 | 360, det lower −14 mm |
| 022 | 60 | −20 | 38 | 450 |

Mis-orientation results are as follows:
Sample 4, Location 1, Off 9.4°
Sample 4, Location 2, Off 23.5°
Sample 4, Location 3, Off 10.2°
Sample 4, Location 4, Off 13.8°

Based on this analysis, a fixed point detector approach is disclosed. Two detectors may be set at fixed angular positions corresponding to the (002) and (022) diffraction angular positions. The X value of the diffraction spots will be deduced from Y values and other pre-set parameters, and the Y value of the diffraction spots can be obtained by a slit scanning apparatus.

Figure 13:
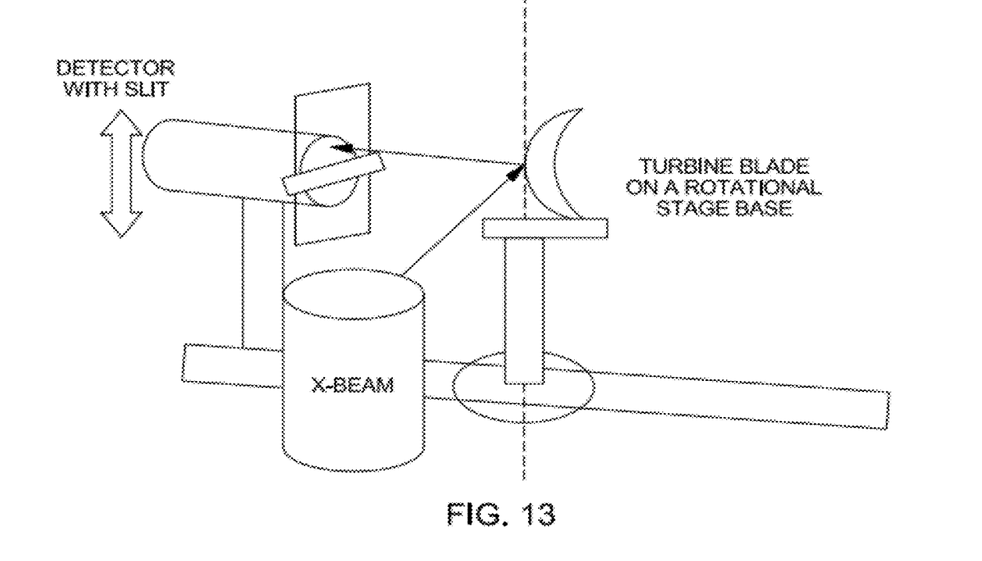
FIG. 13 is a schematic of an XRD analyzer schematic having a point detector with a slit, and rotating sample, for turbine blade grain orientation measurement, in accordance with the present invention.

In this approach, an exemplary NaI detector can be set at either (002) 2-θ 81° position or (022) 2-θ 133° position, adjusted through a rotational scanning mechanism. For the turbine blade initial scanning, the detector will be set as close as possible to the sample with its full active area for the maximum capture solid angle. After the diffraction spots are located, a detector cap with a 2-5 mm horizontal slit can be added to the detector head, and the detector can be scanned vertically to locate the diffraction profile maximum Y positions, which have the major impact to the grain orientation vector. The turbine blade sample will only have an α angular scan, and only the Δα and the Y positions for the two diffraction spots will be combined with other preset parameters or deduced values to calculate the grain orientation in the turbine based coordinate system. FIG. 13 illustrates an embodiment of a fixed detector prototype system for turbine blade grain orientation measurement, in accordance with this aspect of the present invention.

The present invention can be included in an article of manufacture (e.g., one or more computer program products) having, for instance, computer usable media. The media has embodied therein, for instance, computer readable program code means for providing and facilitating the capabilities of the present invention. The article of manufacture can be included as a part of a computer system or sold separately.

Additionally, at least one program storage device readable by a machine embodying at least one program of instructions executable by the machine to perform the capabilities of the present invention can be provided.

The flow diagrams and steps depicted herein are just examples. There may be many variations to these diagrams or the steps (or operations) described therein without departing from the spirit of the invention. For instance, the steps may be performed in a differing order, or steps may be added, deleted, or modified. All of these variations are considered a part of the claimed invention.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the following claims.

What is claimed is:

1. An x-ray diffraction apparatus for measuring crystal orientation of a multiple grain sample, comprising:
    an x-ray excitation path having a focusing optic for collecting x-rays from an x-ray source and redirecting the collected x-rays into an x-ray beam converging on a single grain of the multiple grain sample;
    a first point detector;
    means for rotating the first point detector and sample relative to each other; and
    means for determining a grain orientation based upon diffraction patterns from first and second grain crystal planes within the sample.

2. The apparatus of claim 1, further comprising:
    a second point detector, wherein the first point detector collects a diffraction pattern from the first crystal plane, and the second point detector collects a diffraction pattern from the second crystal plane.

3. The apparatus of claim 1, further comprising:
    a rotation stage upon which the sample is placed, to facilitate collection of diffraction patterns from the first and second crystal planes by the first point detector.

4. The apparatus of claim 1, further comprising:
    a rotation stage upon which the first point detector is mounted, to facilitate collection of diffraction patterns from the first and second crystal planes by the first point detector.

5. The apparatus of claim 1, wherein the focusing optic comprises a polycapillary optic, having an output focused beam spot size of about 300 μm or smaller.

6. The apparatus of claim 1 in combination with the sample, the sample comprising a turbine blade.

7. An x-ray diffraction method for measuring crystal orientation of a multiple grain sample, comprising:
    using a focusing optic for collecting x-rays from an x-ray source and redirecting the collected x-rays into an x-ray beam converging on a single grain of the multiple grain sample;
    using a first point detector to collect at least first and second grain crystal planes by rotating the detector and sample relative to each other; and
    determining a grain orientation based upon diffraction patterns collected from first and second grain crystal planes.

8. The method of claim 7, further comprising:
    using the first point detector to collect a diffraction pattern from the first crystal plane; and
    using a second point detector to collect a diffraction pattern from the second crystal plane.

9. The method of claim 7, further comprising:
    rotating the sample, to facilitate collection of diffraction patterns from the first and second crystal planes by the first point detector.

10. The method of claim 7, further comprising:
    rotating the first point detector to facilitate collection of diffraction patterns from the first and second crystal planes by the first point detector.

11. The method of claim 7, wherein the focusing optic comprises a polycapillary optic, having an output focused beam spot size of about 300 μm or smaller.

12. The method of claim 7 wherein the sample comprises a turbine blade.

* * * * *